US012041979B2

(12) United States Patent
Roy

(10) Patent No.: US 12,041,979 B2
(45) Date of Patent: Jul. 23, 2024

(54) CONVERTIBLE NURSING GARMENT

(71) Applicant: TARGET BRANDS, INC., Minneapolis, MN (US)

(72) Inventor: Jennifer Roy, West Lakeland, MN (US)

(*) Notice: Subject to any disclaimer, the term of this patent is extended or adjusted under 35 U.S.C. 154(b) by 186 days.

(21) Appl. No.: 17/676,331

(22) Filed: Feb. 21, 2022

(65) Prior Publication Data

US 2023/0263243 A1    Aug. 24, 2023

(51) Int. Cl.
*A41C 3/04* (2006.01)
*A61M 1/06* (2006.01)

(52) U.S. Cl.
CPC ............... *A41C 3/04* (2013.01); *A61M 1/062* (2014.02)

(58) Field of Classification Search
CPC ................................ A41C 3/04; A61M 1/062
USPC ........................................................... 450/36
See application file for complete search history.

(56) References Cited

U.S. PATENT DOCUMENTS

| | | |
|---|---|---|
| 1,361,155 A | 12/1920 | Jackson |
| 1,990,322 A | 2/1935 | Goldberg |
| 2,501,860 A | 3/1950 | Becker |
| 2,679,048 A | 5/1954 | Alberts |
| 3,175,559 A | 3/1965 | Kane |
| 4,390,024 A | 6/1983 | Williams |
| 4,564,015 A | 1/1986 | Friedman |
| 4,648,404 A | 3/1987 | Clark |
| 4,911,677 A | 3/1990 | White |
| 5,269,720 A | 12/1993 | Moretz et al. |
| 5,385,502 A | 1/1995 | Moretz et al. |
| 5,514,166 A | 5/1996 | Silver et al. |
| 5,575,768 A | 11/1996 | Lockridge et al. |
| 5,611,086 A | 3/1997 | Eggen |
| 6,004,186 A | 12/1999 | Penny |
| 6,213,840 B1 | 4/2001 | Han |

(Continued)

FOREIGN PATENT DOCUMENTS

WO    2009081400 A2    7/2009
WO    2009137223 A2    11/2009

OTHER PUBLICATIONS

"LLLI Patented Hands-Free Pumping & Nursing Bra", publicly offered for sale by La Leche League International at www.llli.com at least as early as Dec. 2011 (1 page).

(Continued)

*Primary Examiner* — Timothy K Trieu
(74) *Attorney, Agent, or Firm* — Griffiths & Seaton PLLC; JoAnn M. Seaton

(57) ABSTRACT

A nursing garment is configured to be worn by a wearer having breasts and for use with a pumping apparatus and includes a band, a pair of inner soft cups, and an exterior front panel. The band extends around a torso of the wearer. The pair of inner soft cups are secured to the band, and each includes a top retaining panel and a bottom retaining panel overlapping one another. The top retaining panel and the bottom retaining panel are configured to be selectively pulled away from each other forming an opening therebetween to permit a portion of the pumping apparatus to extend through the opening during milk expression. The exterior front panel extends over the pair of inner soft cups having a bottom edge that is free from mid-length securement can be at least partially pulled upwardly to expose one or both of the pair of inner soft cups.

22 Claims, 14 Drawing Sheets

(56) References Cited

U.S. PATENT DOCUMENTS

| | | |
|---|---|---|
| 6,227,936 B1 | 5/2001 | Mendoza |
| 6,247,996 B1 * | 6/2001 | Fields .................. A41C 3/04 |
| | | 450/36 |
| 6,346,027 B1 | 2/2002 | Merkovsky |
| 6,361,398 B1 | 3/2002 | Knapp |
| 6,786,798 B1 | 9/2004 | Gendel |
| 6,821,185 B1 | 11/2004 | Francis |
| 6,839,908 B2 | 1/2005 | Schneider et al. |
| 6,855,029 B2 | 2/2005 | Rothman |
| D505,243 S | 5/2005 | Thunstedt |
| 6,974,361 B2 | 12/2005 | Cravaack et al. |
| 6,983,489 B2 | 1/2006 | Caprio |
| D523,212 S | 6/2006 | Iourina |
| 7,077,720 B2 | 7/2006 | Schneider et al. |
| 7,081,034 B1 | 7/2006 | Zoellner |
| 7,094,217 B2 | 8/2006 | Fialkoff |
| 7,448,090 B2 | 11/2008 | Lucock |
| D625,487 S | 10/2010 | Hendrickson |
| 7,878,880 B2 | 2/2011 | Hendrickson |
| 7,878,881 B2 | 2/2011 | Hendrickson |
| 7,946,904 B1 | 5/2011 | Ciullo |
| 7,950,980 B2 | 5/2011 | Solberg et al. |
| D644,003 S | 8/2011 | Hendrickson |
| 8,057,452 B2 | 11/2011 | Fialkoff |
| 8,075,369 B2 | 12/2011 | Hendrickson |
| 8,137,153 B2 | 3/2012 | Bell |
| 8,147,291 B2 | 4/2012 | Hirtz |
| 8,192,247 B2 | 6/2012 | Abbaszadeh |
| 8,226,452 B2 | 7/2012 | Hendrickson |
| 8,307,463 B2 | 11/2012 | Ritchie |
| 8,323,070 B2 | 12/2012 | Abbaszadeh |
| 8,469,769 B2 | 6/2013 | Hendrickson |
| 8,469,770 B2 | 6/2013 | Alva |
| 9,113,660 B2 | 8/2015 | Op'T Hof |
| 9,167,855 B2 | 10/2015 | Abbaszadeh |
| 9,402,425 B2 | 8/2016 | Cortese et al. |
| 9,498,005 B2 | 11/2016 | Abbaszadeh |
| 9,591,878 B2 | 3/2017 | Applewhite |
| 9,826,785 B2 | 11/2017 | Blacker |
| D854,782 S | 7/2019 | Ironi |
| 10,405,587 B2 | 9/2019 | Cortese et al. |
| 10,420,377 B2 | 9/2019 | Abbaszadeh |
| 2003/0027491 A1 | 2/2003 | Cravaack et al. |
| 2004/0038621 A1 | 2/2004 | Vera |
| 2004/0143885 A1 | 7/2004 | Rothman |
| 2004/0198176 A1 | 10/2004 | Dutka et al. |
| 2005/0026540 A1 | 2/2005 | Schneider et al. |
| 2005/0085160 A1 | 4/2005 | Johnstone |
| 2007/0074330 A1 | 4/2007 | Azaronak |
| 2007/0161330 A1 | 7/2007 | Whitehead et al. |
| 2007/0271675 A1 | 11/2007 | Eraca |
| 2008/0022434 A1 | 1/2008 | Adelman |
| 2008/0229474 A1 | 9/2008 | Fons et al. |
| 2009/0036022 A1 | 2/2009 | Tolliver |
| 2009/0265831 A1 | 10/2009 | Hendrickson |
| 2009/0282603 A1 | 11/2009 | Kumar |
| 2009/0286452 A1 | 11/2009 | Grayson |
| 2010/0031418 A1 | 2/2010 | Op'T Hof |
| 2010/0058512 A1 | 3/2010 | Rothman |
| 2010/0068971 A1 | 3/2010 | Hendrickson |
| 2010/0068972 A1 | 3/2010 | Hendrickson |
| 2010/0159801 A1 | 6/2010 | Abbaszadeh |
| 2010/0159802 A1 | 6/2010 | Abbaszadeh |
| 2011/0081826 A1 | 4/2011 | Hendrickson |
| 2011/0219513 A1 | 9/2011 | Hendrickson |
| 2011/0237156 A1 | 9/2011 | Boonen et al. |
| 2011/0314587 A1 | 12/2011 | Ritchie |
| 2013/0095727 A1 | 4/2013 | Abbaszadeh |
| 2013/0232661 A1 | 9/2013 | Huntley |
| 2015/0038051 A1 | 2/2015 | Fisher et al. |
| 2015/0143605 A1 | 5/2015 | Cobb |
| 2016/0007659 A1 | 1/2016 | Blacker |
| 2016/0015092 A1 | 1/2016 | Abbaszadeh |
| 2017/0280786 A1 | 10/2017 | Abbaszadeh |
| 2018/0103691 A1 * | 4/2018 | Alva .................. A41C 3/04 |
| 2020/0154792 A1 | 5/2020 | Abbaszadeh |
| 2021/0345690 A1 * | 11/2021 | Stanton .................. A41C 3/04 |

OTHER PUBLICATIONS

"Milkalicious Double Cream Nursing Tank", printed from www.milkalicious.com/Milkalicious_Double_Cream_Nursing_Tank_p/milk-tank.htm available at least as early as Jun. 9, 2012 and additional product pictures (3 pages).

"Hands-Free Pumping Bra", printed from www.amazon.com/Hands-Free-Breastfeeding-Adjustable-Wire-Free-Suitable/dp/B07SK641J3, publicly available at least as early as May 29, 2019 (11 pages).

"Ollie Gray Bra", printed from https://olliegraybras.com/pages/our-bra, publicly available at least as early as Mar. 19, 2019, per http://web.archive.org (7 pages).

* cited by examiner

CONVERTIBLE NURSING GARMENT

BACKGROUND OF THE INVENTION

The benefits of nourishing newborn infants by breastfeeding have long been established. Nursing mothers today are increasingly busy and for various reasons often wish to express breast milk to store for times when she is unable or unavailable to directly breast feed her infant or for modesty, convenience, or other reasons prefers not to directly breast feed her infant. A mother, or milk donor, typically expresses breast milk using an electric or manual pumping device in connection with a funnel or shield that is held tightly over the woman's breast. The pumping device creates suction inducing milk flow and directing the flow of milk through the shield and to a storage container coupled to the pumping device.

To save time, a mother or milk donor often expresses milk from both breasts simultaneously, which generally requires the individual to hold the shields using both hands against the breasts, leaving the individual unable to enjoy other activities requiring use of their hands. The process of expressing milk can be time consuming, and consequently, there is a need for garments that assist in holding the shields tightly against an expresser's breasts during milk expression while freeing their hands for other activities. Existing garments for this purpose largely are configured to be worn only during periods when milk is being expressed, thereby, requiring a garment change before and after expressing milk, which increases the burden on the individual expressing milk. Accordingly, there continues to be a need for garments that both assist a wearer in expressing milk and provide the support and/or style desired by the wearer during periods between milk expressing sessions.

SUMMARY

One aspect of the present invention relates to a nursing garment configured to be worn by a wearer having breasts and for periodic use with a pumping apparatus. The nursing garment includes a band, a pair of inner soft cups, and an exterior front panel. The band is configured to extend around a torso of the wearer below the breasts. The pair of inner soft cups are secured near a top edge of the band, wherein each of the pair of inner soft cups includes a top retaining panel and a bottom retaining panel, which is separate from the top retaining panel, overlapping one another across a substantially horizontal length of a corresponding one of the pair of inner soft cups. The top retaining panel and the bottom retaining panel are configured to be selectively pulled away from each other to form an opening therebetween in a manner permitting a portion of the pumping apparatus to extend through the opening facilitating expression of milk from the breast via the pumping apparatus. The exterior front panel extends over the pair of inner soft cups and defines a bottom edge that is free from mid-length securement such that the exterior front panel is configured to selectively be at least partially pulled upwardly away from the band to expose one or both of the pair of inner soft cups. Other apparatus, assemblies, and associated methods are also disclosed.

BRIEF DESCRIPTION OF THE DRAWINGS

Embodiments of the invention will be described with respect to the figures, in which like reference numerals denote like elements, and in which.

DETAILED DESCRIPTION

This innovation relates to a garment for wear by a nursing mother to assist in expressing milk in a manner leaving the mother's hands free for use during milk expression, even when simultaneously expressing from both of the mother's breasts. The garment provides breast support and style to the mother such that the garment is suitable for wear by the mother during periods of non-breast feeding or milk expression. By providing a single garment that can be used for normal wear support, for maintaining a pump device shield in proper contact with a breast during milk expression, and/or for direct infant nursing, a mother does not need to change their bra or undergarment to separately allow for each of these activities, saving busy mothers some much-needed time.

Figure 1:
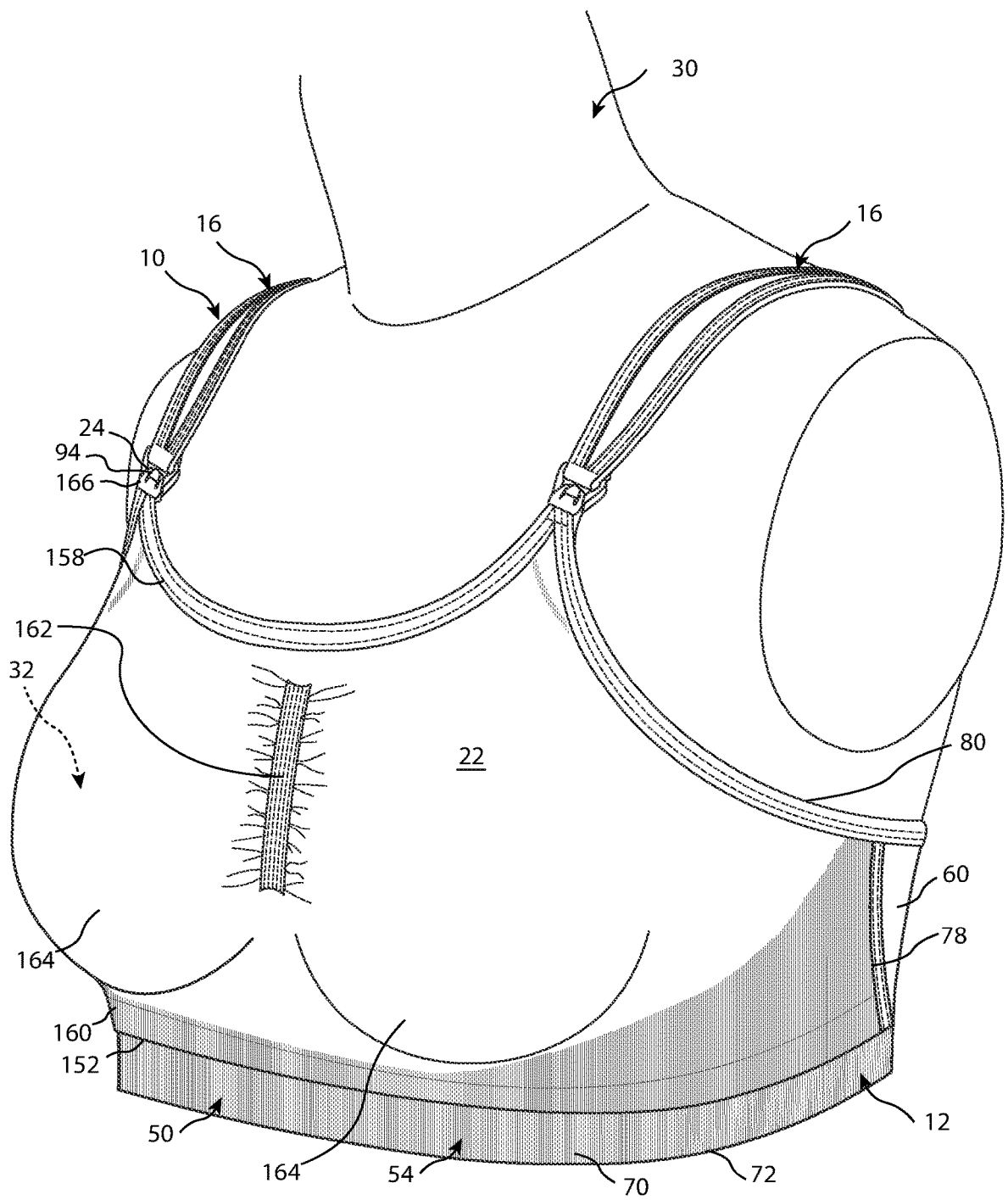
FIG. 1 is a front perspective view illustration of a nursing garment in a normal wear configuration, according to one embodiment of the present invention.
Figure 2:
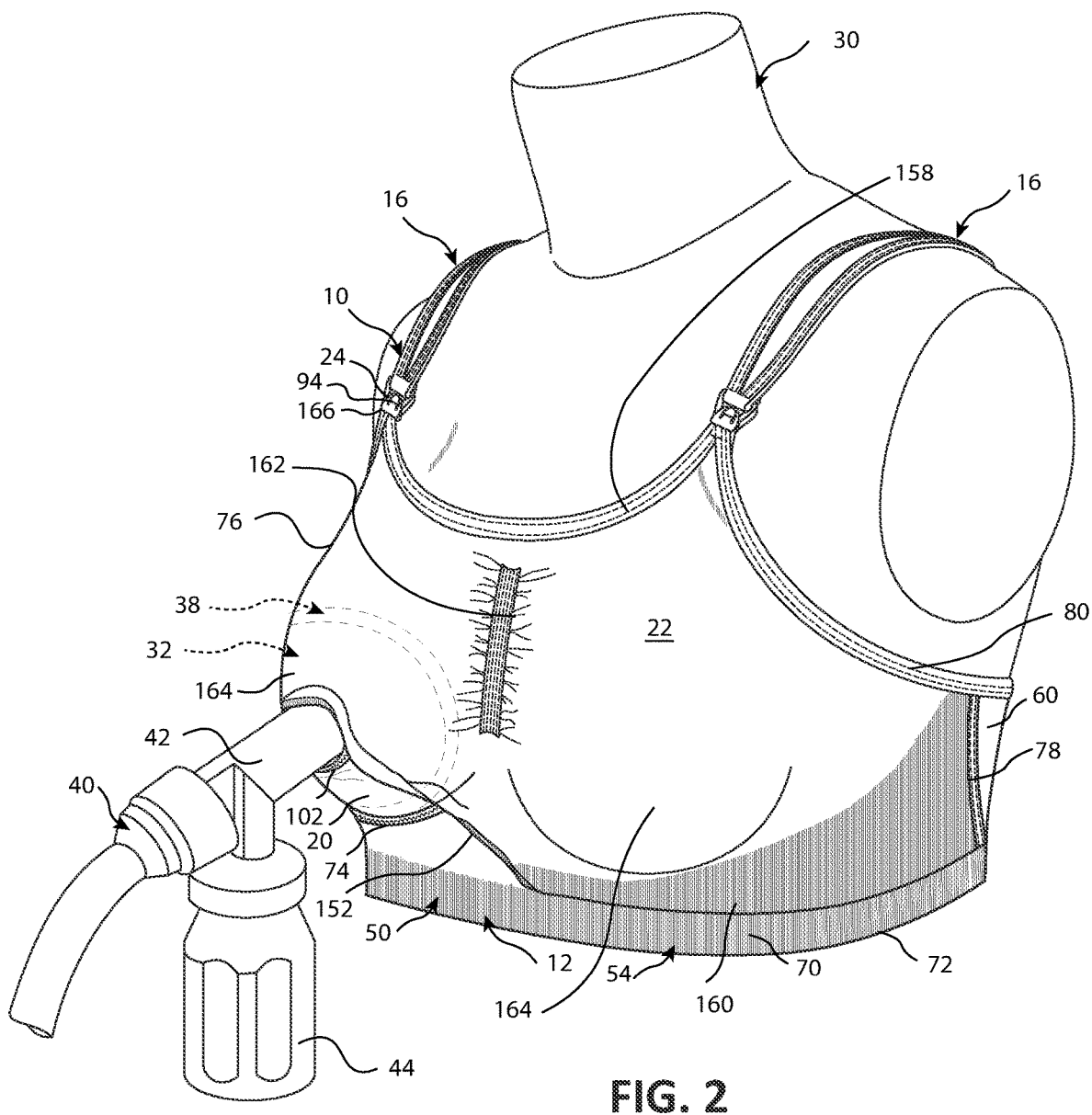
FIG. 2 is a front perspective view illustration of a nursing garment in a pumping configuration, according to one embodiment of the present invention.
Figure 3:
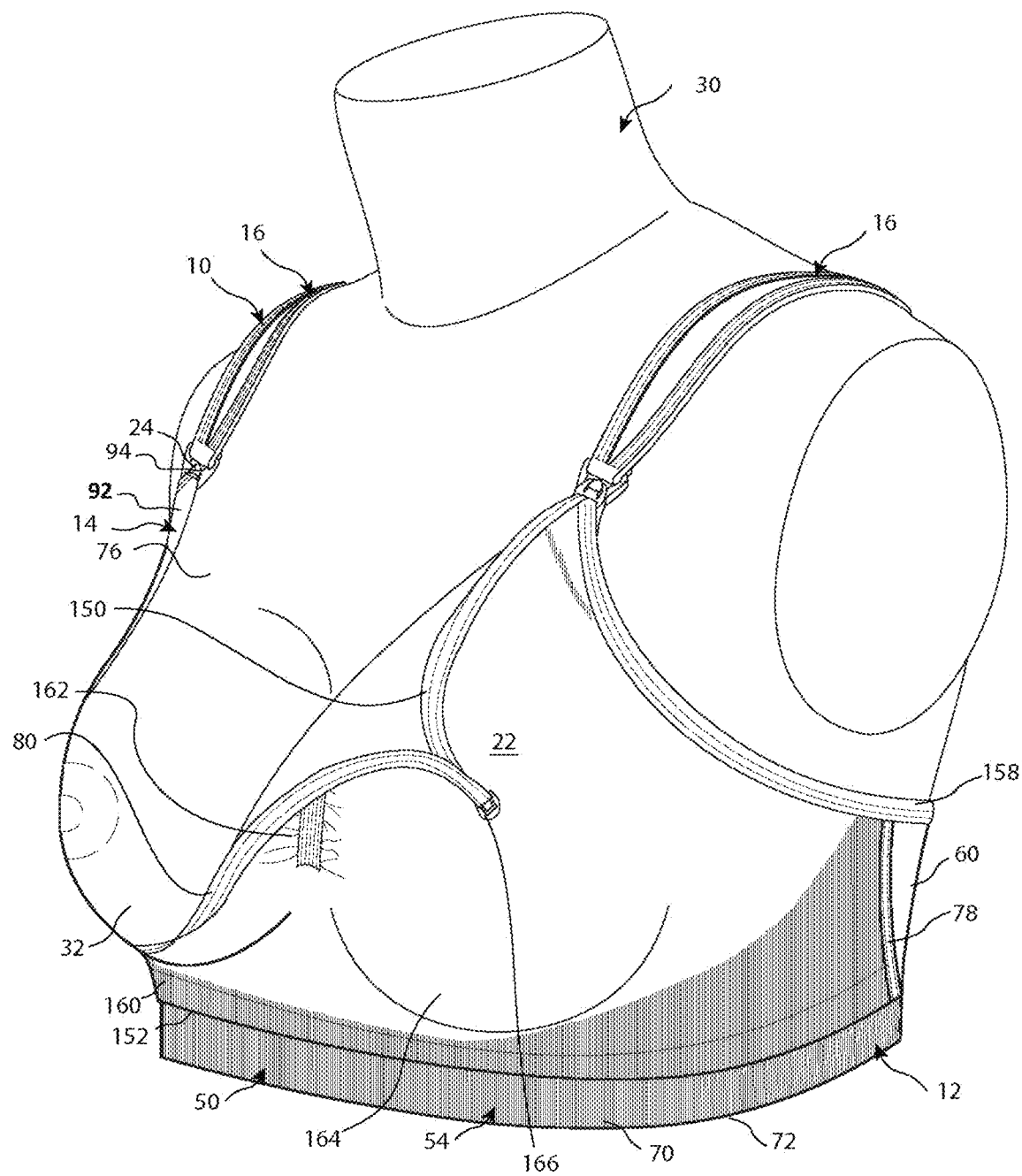
FIG. 3 is a front perspective view illustration of a nursing garment in a breast-feeding configuration, according to one embodiment of the present invention.
Figure 4:
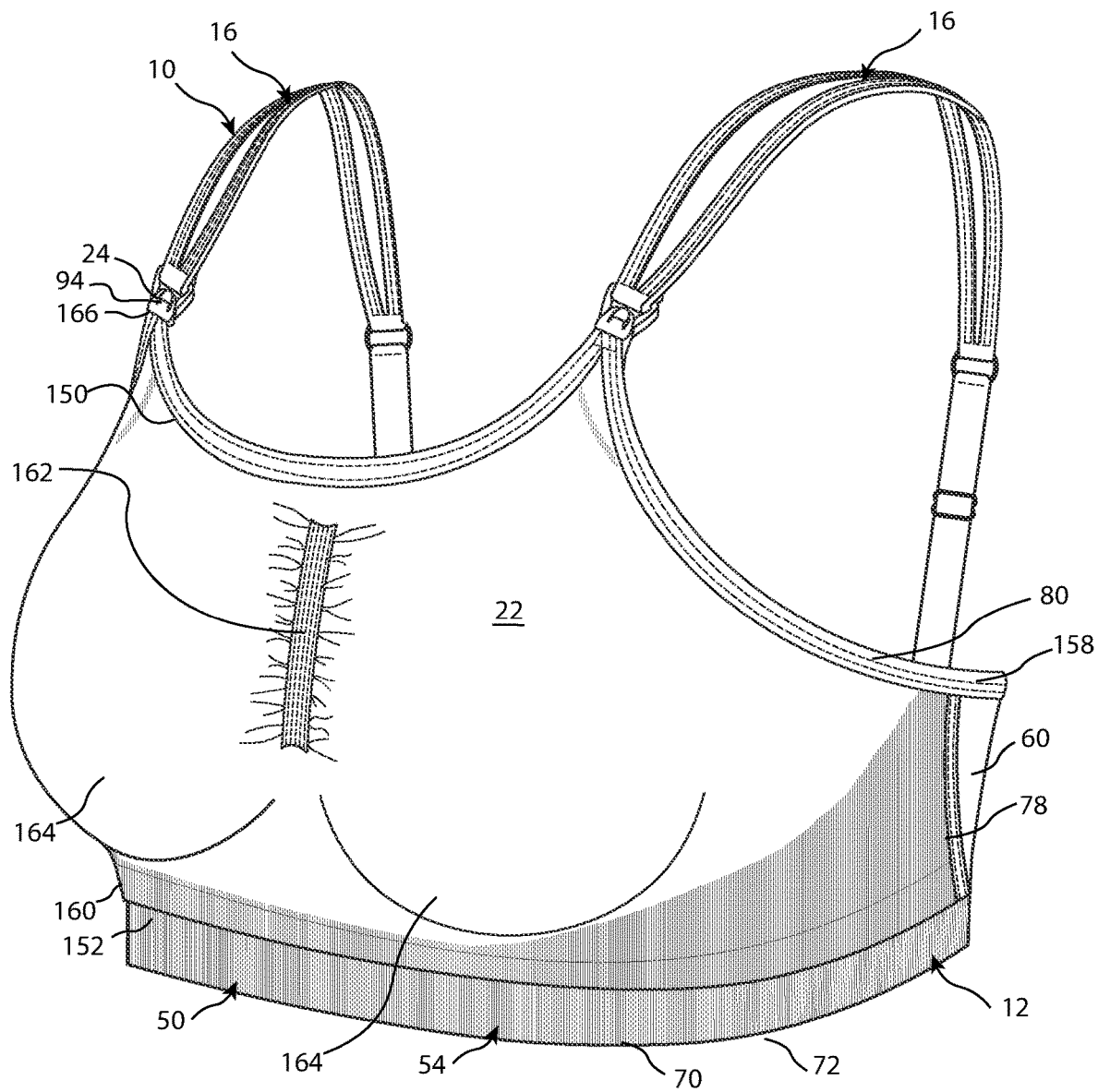
FIG. 4 is a front perspective view illustration of the nursing garment of FIG. 1 in a normal wear configuration, according to one embodiment of the present invention.
Figure 5:
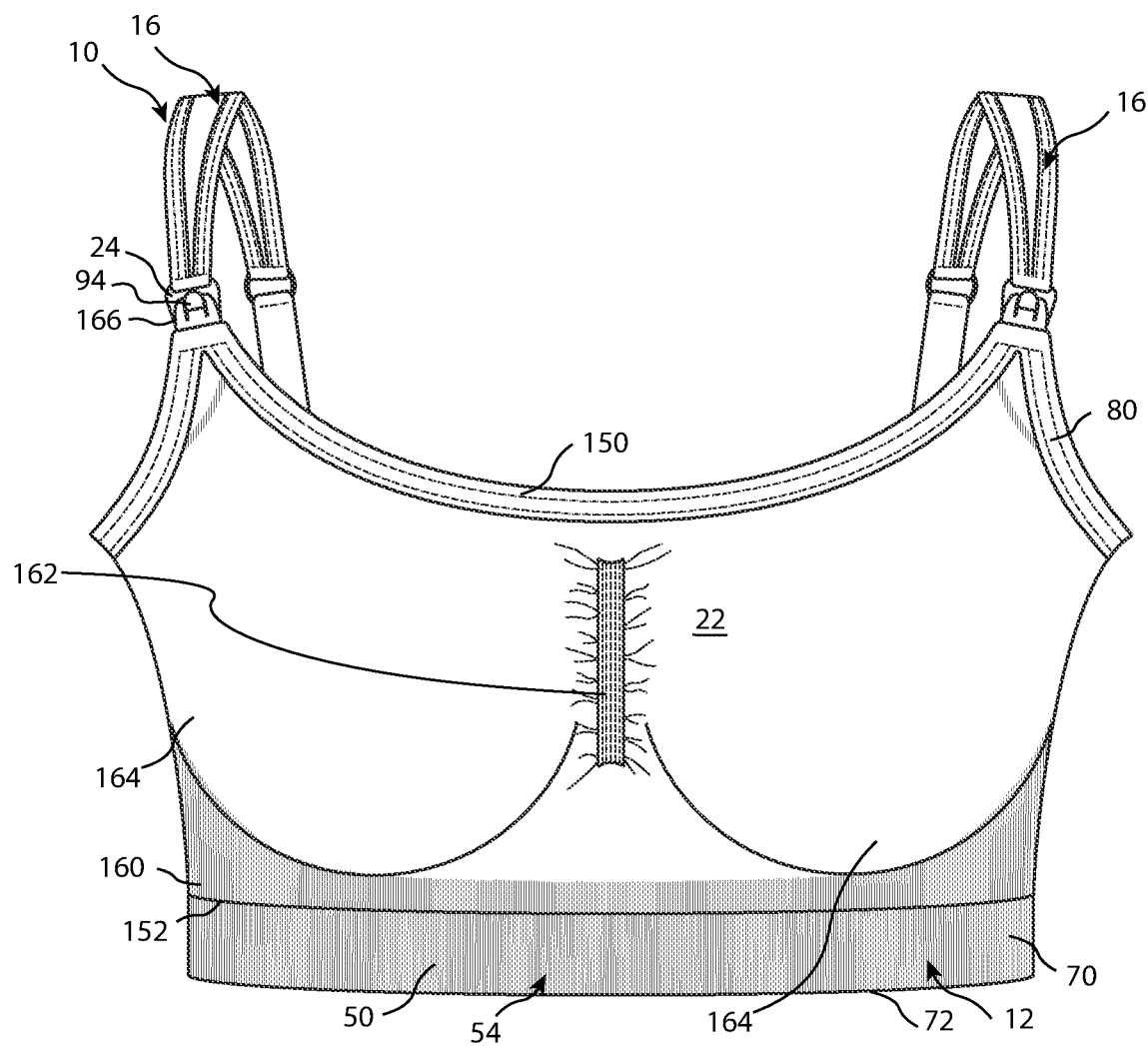
FIG. 5 is a front view illustration of the nursing garment of FIG. 4 in the normal wear configuration, according to one embodiment of the present invention.
Figure 14:
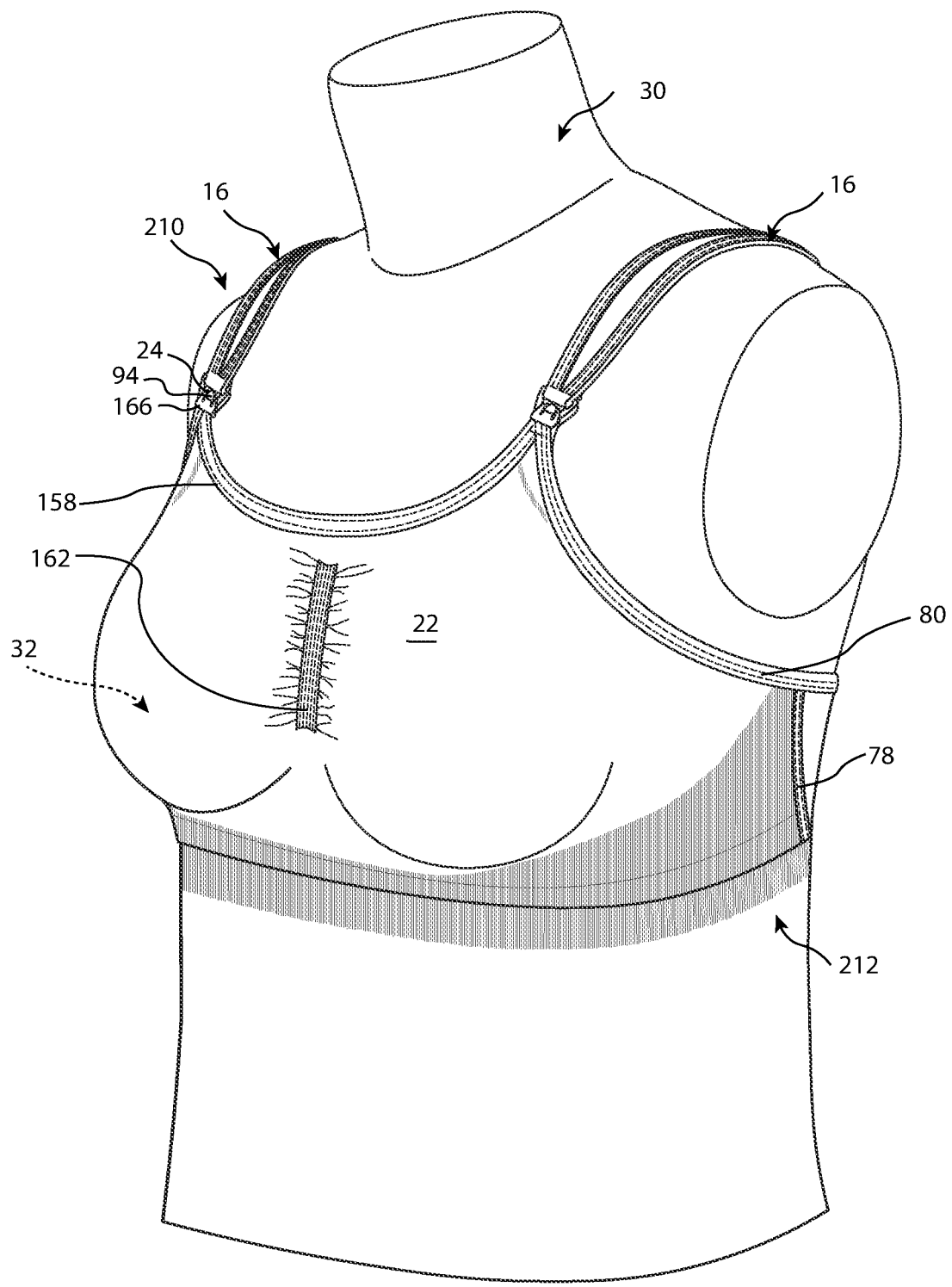
FIG. 14 is a front perspective view illustration of a nursing garment in a normal wear configuration, according to one embodiment of the present invention.

Generally referring to FIGS. 1-3, the present invention, uses a three-layer front construction to form the garment, for example, a brassiere (for example, as shown in FIGS. 1-4) or a camisole (for example, as shown in FIG. 14). The nursing garment includes a band encircling a torso of a wearer under the breasts of the wearer. In one embodiment, a first or interior layer includes retention straps extending upwardly from the band and fitting immediately adjacent opposing sides of the wearer's breasts The second or intermediate layer includes a pair of soft cups configured to stretch to accommodate the wearer's breasts as required for various stages during a nursing schedule (for example, a woman's breasts may be one size following nursing or milk expression but swell to a larger size just before subsequent nursing or milk expression) in one embodiment.

Each of the pair of soft cups us formed by a top retention panel and a bottom retention panel overlapping each other in a substantially horizontal manner, that is, at an angle less than 45° offset from a parallel orientation with a bottom of the band, across a middle third portion of the corresponding soft cup of the pair or soft cups, in one example. In one embodiment, the stretchable nature of each of the soft cups, allows top and bottom panels to be separated along their overlap to form an opening, e.g., a substantially horizontal opening, therebetween for receiving a portion of the pumping apparatus, e.g., to hold of shield of the pumping apparatus against a breast of the wearer with the neck extending from the shield extending through the opening.

The third layer includes an exterior front panel made of an elastic and stretchable material covering the pair of soft cups while in a normal wear configuration and being free along a bottom edge thereof. The exterior front panel can be pulled upwardly from the bottom edge thereof to expose the pair of soft cups in a pumping configuration. In one embodiment, the second and third layers selectively couple to a top of the retention strap to be held over the breasts of the wearer in the normal wear and pumping configurations. Second and third layers are uncoupled from the top of the retention strap and folded downwardly to expose the first layer, that is the retention strap and the breast(s) of the wearer in a nursing configuration. In this manner, the nursing garment is configured for multiple uses of a wearer along one such garment to be suitable for normal wear, pumping, and nursing increasing each of wear and comfort to the wearer. In one example the various portions of the nursing garment are all formed of a continuous or seamless knit or similar fabric. Other nursing garments and/or variations thereof are also described in examples below.

Turning to the figures, FIGS. 1-3 illustrate examples of various configurations of a nursing garment 10, that is, showing nursing garment 10 in examples of a normal wear configuration, a pumping configuration, and a breast-feeding configuration, respectively. As used throughout this application, the term "nursing" should be given broad meaning including direct nursing to an infant or indirect nursing including milk expression from the breasts 32 using a pump or other device. Nursing garment 10 generally includes an encircling band 12, a pair of retention straps 14, a pair of shoulder straps 16, a pair of top retaining panels 18, a pair of bottom retaining panels 20, and exterior front panel 22. In one embodiment, each of band 12, retention straps 14, pair of top retaining panels 18, pair of bottom retaining panels 20 are formed of Each retention strap 14 extends upwardly from band 12 to a corresponding one of shoulder straps 16, which is, in turn, secured to a opposite portion of band 12 to fit over wearer's shoulders thereby maintaining nursing garment 10 in a desired on the torso of wearer 30 to selectively cover breasts 32 as shown in FIGS. 1-3, for example. In one embodiment, each of retention straps 14 extends directly along an outside portion of a different one of breasts 32 to provide some support and/or lift to the corresponding breast 32.

In one embodiment, one of the pair of top retaining panels 18 and a corresponding or mating one of the pair of bottom retaining panels 20 collectively form an inner soft cup 34 coupled to band 12. Each of inner soft cups 34 covers one of the breasts 32 of the wearer 30, as shown with additional reference to FIG. 12. As used herein "soft cups" refer to portions nursing garment 10 that are each configured to stretch to receive breasts 32 but are not pre-formed in a convex manner or padded with a cup shape, for example, similar to a shelf-bra type of support. Top retaining panel 18 and a corresponding bottom retaining panel 20 overlap in a substantially horizontal manner across a center, that is, within a middle third of one of inner soft cups 34. "Substantially horizontal" as used herein refers to an orientation that is less than 45° offset from an orientation that would be parallel with the lower edge 72 of the band 12.

Figure 12:
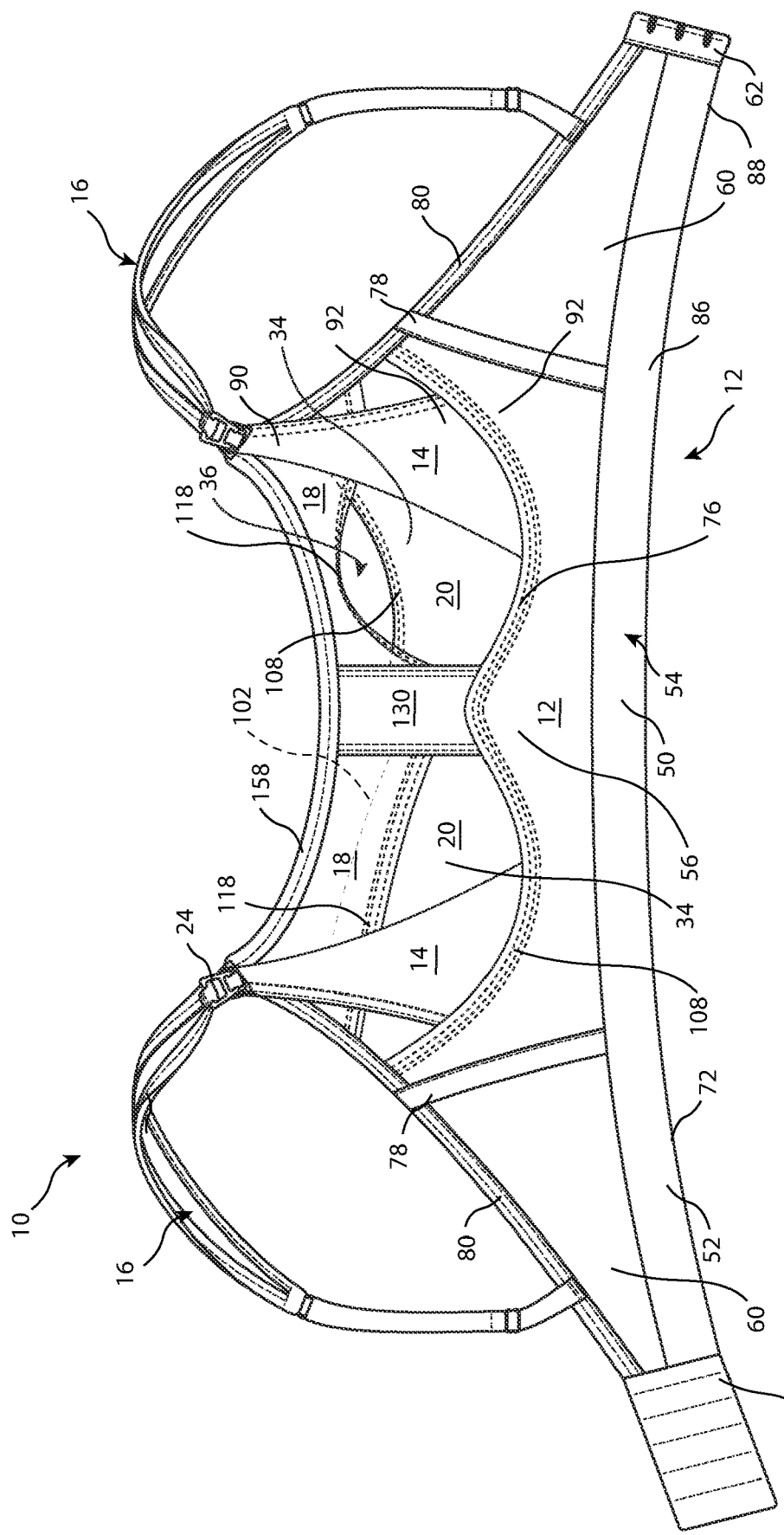
FIG. 12 is a rear view illustration of the nursing garment of FIG. 1 in an open and in a pumping configuration, according to one embodiment of the present invention.

The top retaining panel 18 and the bottom retaining panel 20 overlap in a manner still allowing inner soft cup 34 to split horizontally across inner soft cup 34, as shown on for the inner soft cup 34 at right in FIG. 12, forming a selective slit or opening 36 (see FIG. 12) thereacross. The split of inner soft cup 34 allows inner soft cup 34 to selectively receive a funnel or shield 38 of pump apparatus 38 to hold a shield 38 directly adjacent one of breasts 32 surrounding a nipple thereof such that a neck 42 of shield 38 extends through opening 36 in one of inner soft cups 34 to allow milk expressed from breast 32 to flow to a milk storage container 44, which is selectively coupled to pump apparatus 38. In one embodiment, both top retaining panel 18 and bottom retaining panel 20 are formed with sufficient elastic stretch to expand with as a wearer's breast 32 fill with breast milk and to compressively hold the shield 28 of pump apparatus 40 tightly to the wearer's breast 32 during expression of milk from the wearer's breasts 32 even as the wearer's breasts 32 shrink during that expression.

Exterior front panel 22 is sized and shaped to extend over a substantially entirety of nursing garment 10, in particular, at least entirely over inner soft cups 34 providing modesty and a smooth profile over inner soft cups 34. In one embodiment, exterior front panel 22 extends over a substantial entirety, that is more than 80% of, a front of nursing garment 10 to form a smooth and modest covering overlapping breasts 32. More specifically, exterior front panel 22 is stretchable and defines exterior soft cups 46, which each extend over a different one of inner soft cups 34. Exterior front panel 22 selectively couples to shoulder straps 16 so that exterior front panel 22 can be uncoupled from shoulder strap 16 to fold down exposing breasts 32 as sown in FIG. 3 or, while coupled to shoulder strap 16 exterior front panel 22 can be pulled upwardly exposing one or both of inner soft cups 34 there behind. In view of the above, nursing garment 10 is a functional support garment for breasts 32 during non-nursing periods and converts for expressing and/or direct nursing.

More specifically, in one embodiment, encircling band 12 wraps around and is at least selectively secured to encompass the torso of wearer 30, for example, below breasts 32 (see FIG. 3) of wearer 30 to define a front portion 50 and a rear portion 52 thereof. Front portion 50 includes an under-cup binding 54 continuously extending below inner soft cups 34 and a center gore 56 extending slightly upwardly from under-cup binding 54 between the inner soft cups 34. In one embodiment, rear portion 52 includes two wings 60 and fastener strips 62. Each of the two wings 60 extends rearwardly from an opposing side of under-cup binding 54 to one fastener strip 62. Each of the two fastener strips 62 selectively coupled to each other to hold encircling band closed around torso of wearer 30. In one example, the fastener strips 62 include a hook strip and a loop fastener strip. Accordingly, to one embodiment, under-cup binding 54, center gore 56, and wings 60 are all formed as a single piece of a continuous knit material that is resiliently stretchable and may be woven with elastane fibers such as LYCRA® fibers. In one example, band 12 includes a lower perimeter section 70, adjacent lower edge 72 of band 12, that is woven to have increased elasticity and resiliently in comparison to a remainder of band 12. In one embodiment, a top edge 74 of band 12, opposite lower edge 72, forms a soft "W-shape" with center gore 56 being in a middle portion thereof. Top edge 74 is capped with a binding 76 with or without an underwire, in one example.

One of wings 60 extends outwardly, and, when worn, rearwardly about wearer 30 from an opposing end of under-cup binding 54 to one of fastener strips 62. In this manner, band 12 is selectively coupled to itself via fastener strips 62 to be secured about torso of wearer 30 under breasts 32. In one example, wings 60 and under-cup binding 54 are continuously formed of the same material and/or wings 60 including a lower section 86 woven with increased resiliency and elasticity than a remainder of band 12 adjacent a lower edge 88 thereof to firmly hug wearer 30 about their torso creating a snug, but comfortable fit for wearer 30.

In one example, a length of boning 78 or other stiffener member is coupled to band 12 near the intersection of under-cup binding 54 and wings 60 to provide additional stiffness and support to nursing garment 10 outside of inner soft cups 34. In one embodiment, an underarm binding 80 is sewn to and caps a top edge 74 of band 12, more particularly, of each wing 60 to present a finished edge to nursing garment 60.

Each retention strap 14 is substantially triangular, tapering from a bottom end 90 to a top end 92. Bottom end 90 is sewn to band 12 along top edge 74, for example, partially via binding 76, near an outside portion of the soft "W"-shape. Retention straps 14 are formed a single woven piece of material woven with elasticity and resiliency. In on embodiment, each retention strap 14 is woven with less elasticity that soft cups or center gore 56. Retention strap 14 is configured to provide support to a side of an adjacent breast 32 when nursing garment 10 is worn by wearer 30 and to assist in maintaining nursing garment 10 in place on wear in combination with shoulder straps 16.

Shoulder strap 16, having any suitable configuration and/or padding as desire and as known in the art, is elongated and, in one example, is adjustable in length. Shoulder strap 16 is coupled, for example, is securely sewn to top edge 88 of one of wings 60 at one end and is coupled to top end 82 of retention strap 14 at the opposing end, for instance, via a fastener 24. In one example, fastener 24 is plastic of formed of metal and is configured to selectively receive a secondary fastener 166, as will be further described below.

Inner cups 34 are secured to band 12 along the "W"-shaped portion outside, that is on a side of band 12 opposite wearer 30, as compared to each retention strap 14. In this manner, inner cups 34 are positioned on a side of retention straps 14 opposite breasts 32. As described above, each inner cup 34 is collectively formed by one of top retaining panels 18 and one of bottom retaining panels 20. More specifically, in one example, each of bottom retaining panel 20 includes a curved lower edge 100, an upper edge 102 opposite curved lower edge 100, an inner end 104, and an exterior end 106 opposite inner end 104. The curvature of lower edge 100, in one example, substantially matches the curvature of one side of the "W"-shaped portion of top edge 74 of band 12. Upper edge 102 angles upwardly and outwardly away from inner end 105 and, in one embodiment, is finished to have a portion that remains substantially free, for example, with a binding 108, as will be apparent to those of skill in the art, between inner end 104 and exterior end 106. In one example, upper edge 102 is substantially free when it is free from direct securement to another portion of nursing garment 10 along 65% or more of the length of upper edge 102. In one embodiment, bottom retaining panel 20 is partially sewn directly to top retaining panel 18 near upper edge 102, for example, near opposing ends 104 and 116 thereof in for a length of coupling 122 (see FIG. 6).

In one example, each of top retaining panel 18 includes a top or curved upper edge 110, a lower or bottom free edge 112 opposite curved upper edge 110, an inner end 114, and an exterior end 116 opposite inner end 114, in one embodiment. The curvature of upper edge 110, in one example, is selected to form the profile of a neckline of nursing garment 10. Bottom free edge 112, in one embodiment, has an angled orientation similar to that of upper edge 102 bottom retaining panel 20, for example, angling upwardly and outwardly away from inner end 115. Bottom free edge 112 is finished to remain substantially free, for example, with a binding 118 as will be apparent to those of skill in the art.

Nursing garment 10 includes a first bridge member 130 and a second bridge member 132, in one embodiment. In one example, first bridge member 130 and second bridge member 132 are similarly sized and shaped and are sewn to each other in a manner interposing or sandwiching inner ends 104 of each of the pair of bottom retaining panels 20 and inner ends 114 of each of the pair of top retaining panels 18 therebetween. More specifically, each of first bridge member 130 and second bridge member 132 includes a top edge 134, an opposite, bottom edge 136, and opposing side ends 138 extending substantially parallel to one another.

Each of first bridge member 130 and second bridge member 132 is secured to top retaining panels 18 such that curved upper edges 110 of the top retaining panels 18 align with and symmetrically extend from either side of top edge 134 of first and second bridge members 130 and 132 to collectively define a top neckline shape of nursing garment 10. Each of first bridge member 130 and second bridge member 132 is secured to bottom retaining panels 20 such that curved lower edges 100 of the bottom retaining panels 20 align with and symmetrically extend from either side of bottom edge 136 of first and second bridge members 130 and 132 to collectively form a shape similar to the soft "W"-shape of band 12. When so secured, each bottom retaining panel 20 overlays a different one of top retaining panel 18 such that upper edge 102 of bottom retaining panel 20 extends behind and above bottom free edge 112 of top retaining panel 18, that is such that each bottom retaining panel 20 overlaps one of top retaining panel 18.

Figure 6:
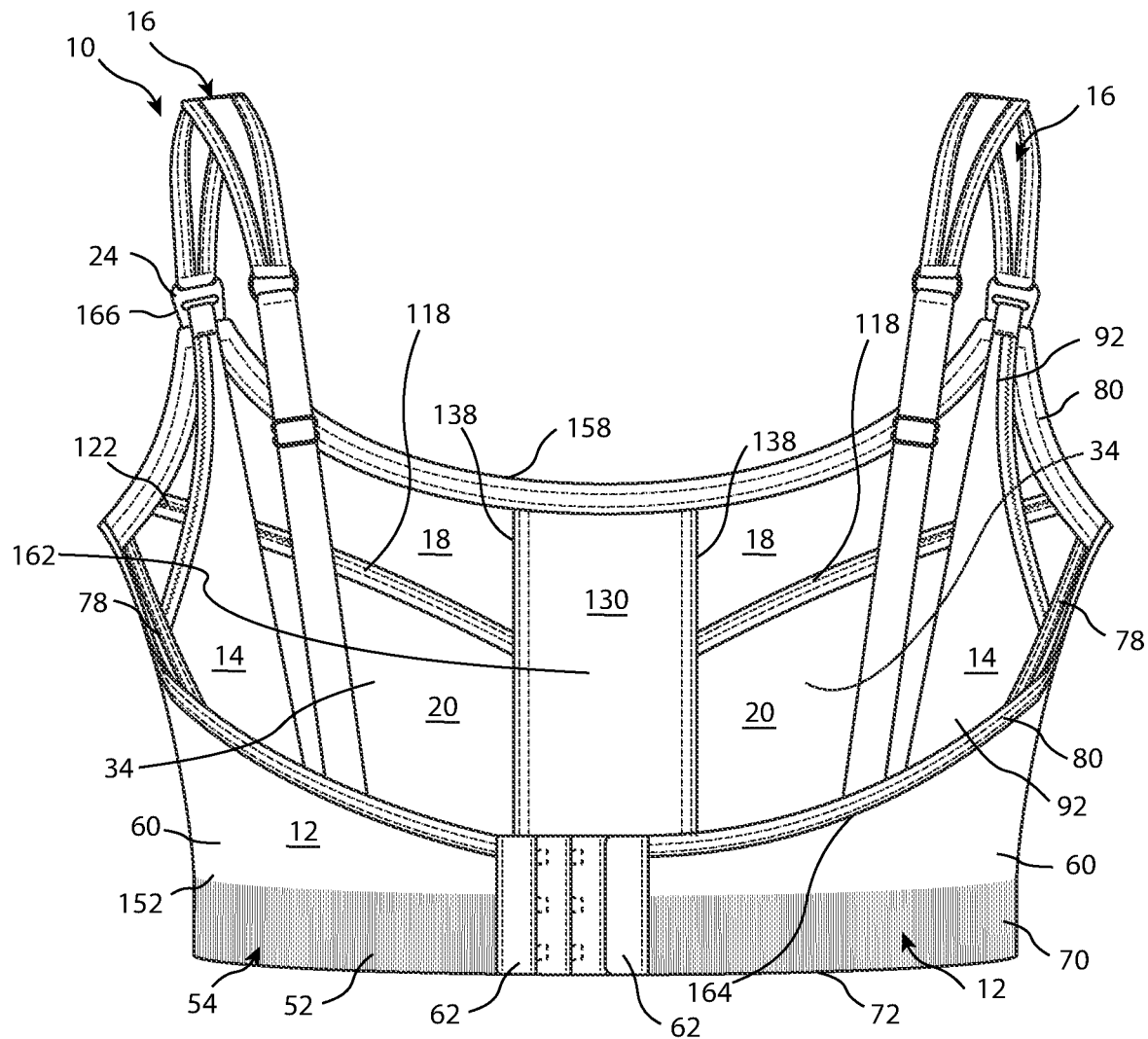
FIG. 6 is a rear view illustration of the nursing garment of FIG. 4 in the normal wear configuration, according to one embodiment of the present invention.
Figure 7:
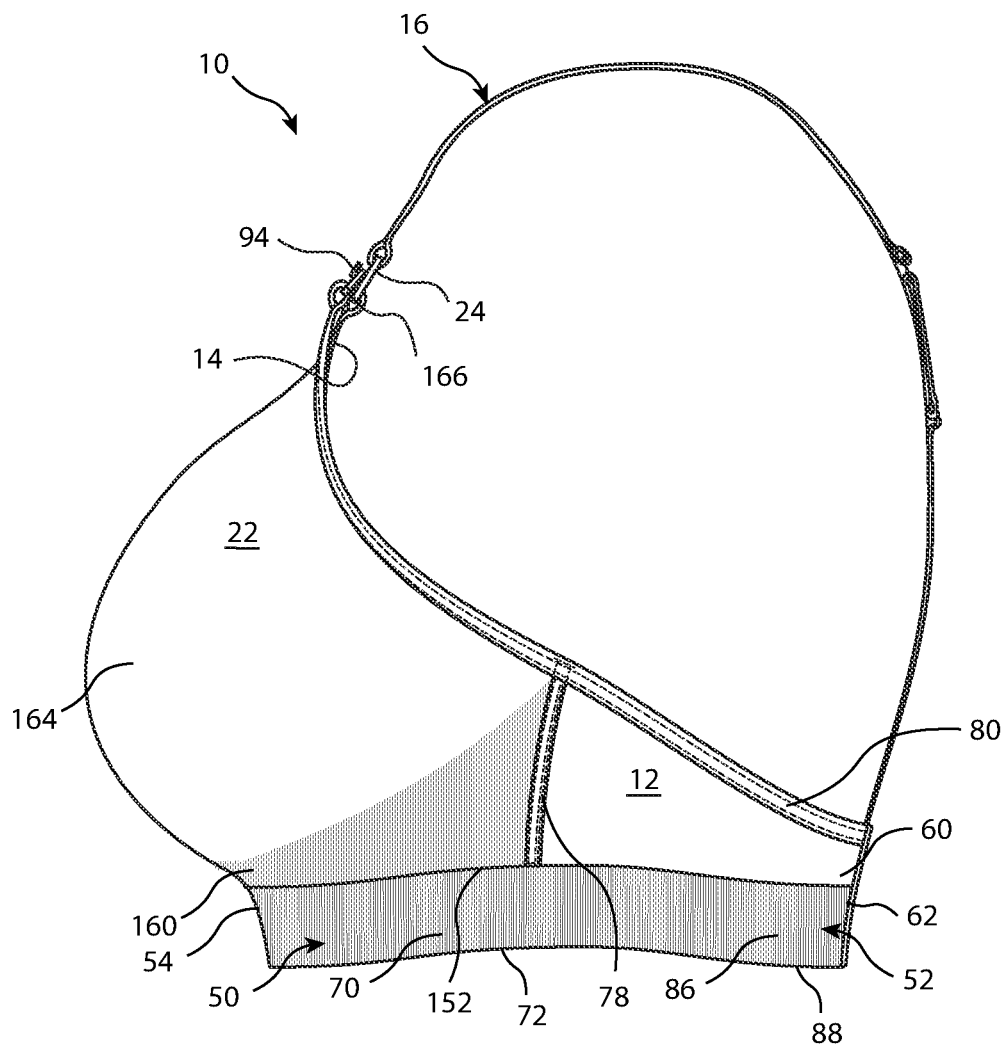
FIG. 7 is a right-side view illustration of the nursing garment of FIG. 4 in the normal wear configuration, according to one embodiment of the present invention.
Figure 8:
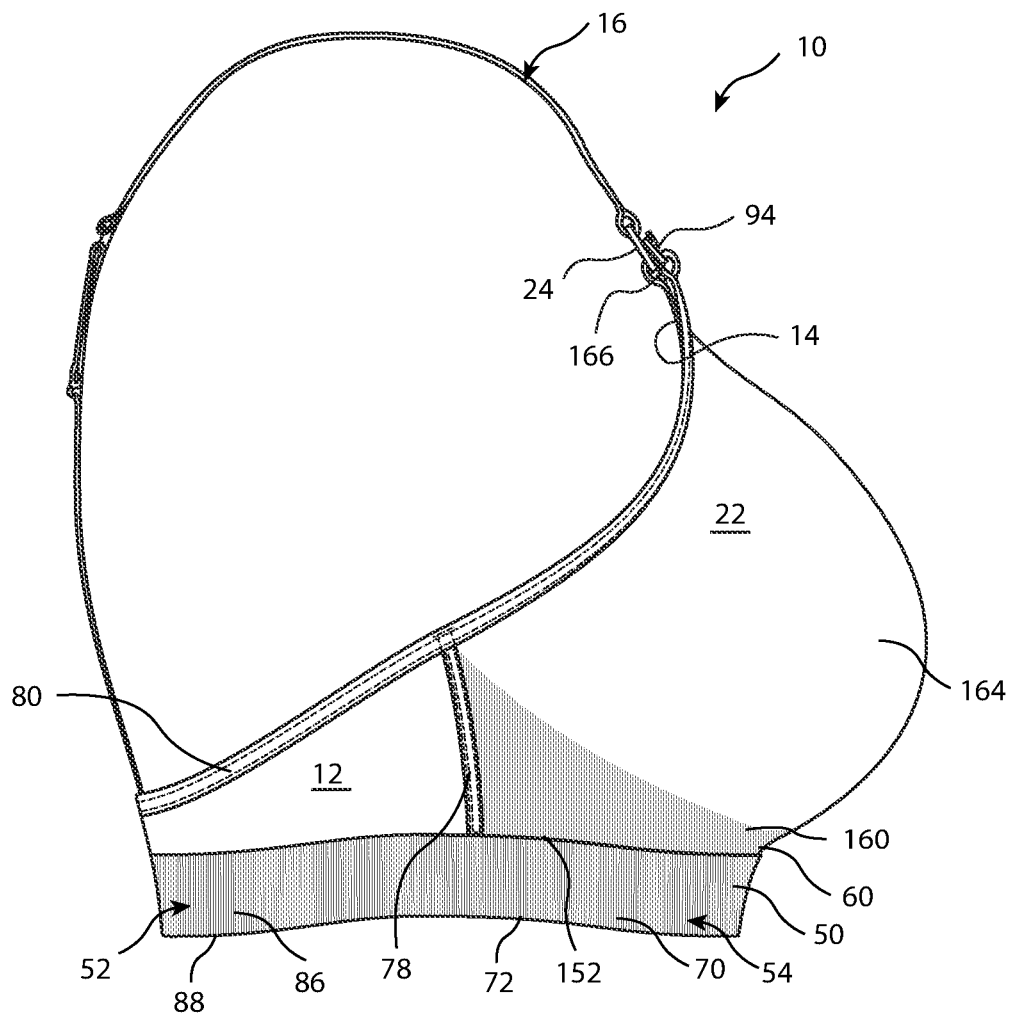
FIG. 8 is a left-side view illustration of the nursing garment of FIG. 4 in the normal wear configuration, according to one embodiment of the present invention.
Figure 9:
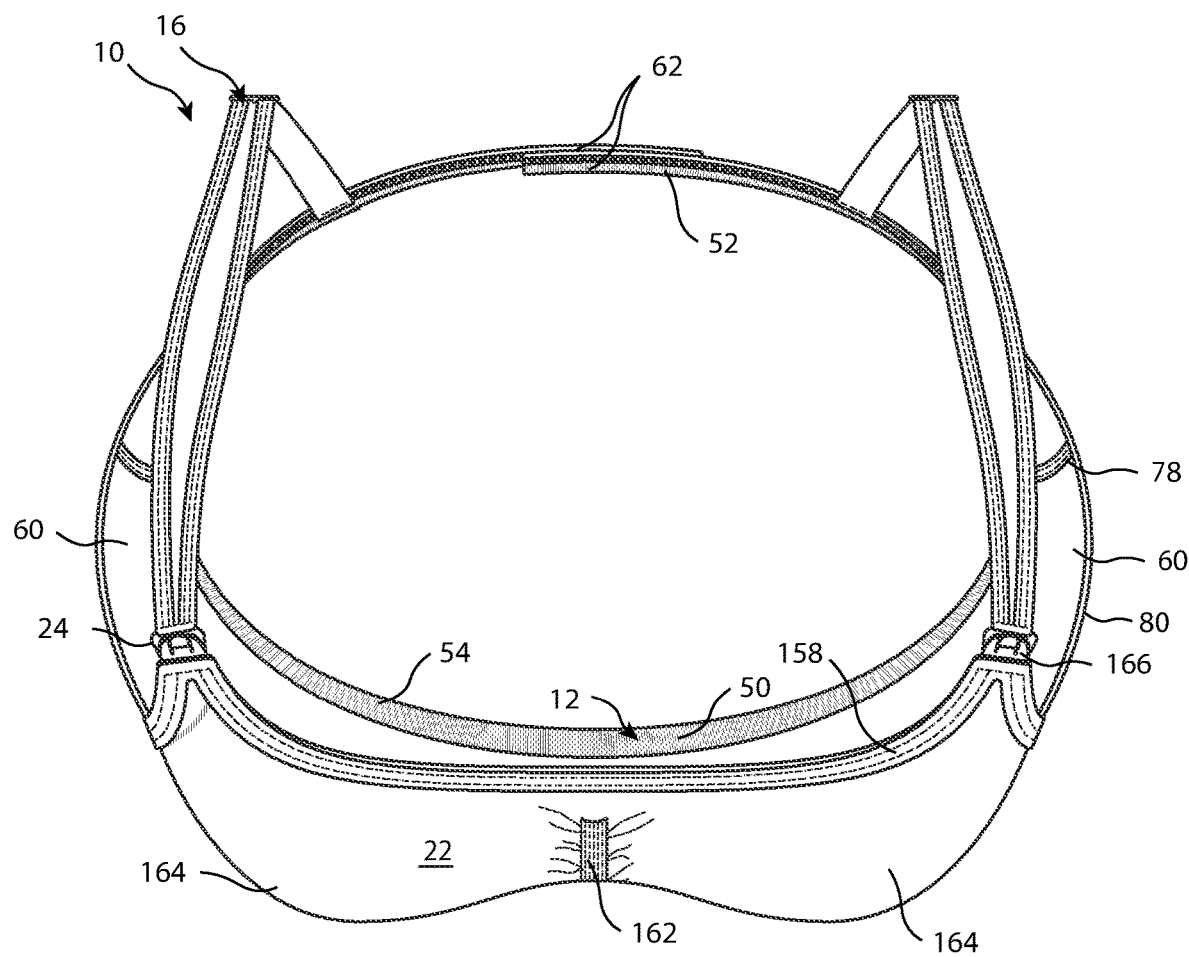
FIG. 9 is a top view illustration of the nursing garment of FIG. 4 in the normal wear configuration, according to one embodiment of the present invention.
Figure 10:
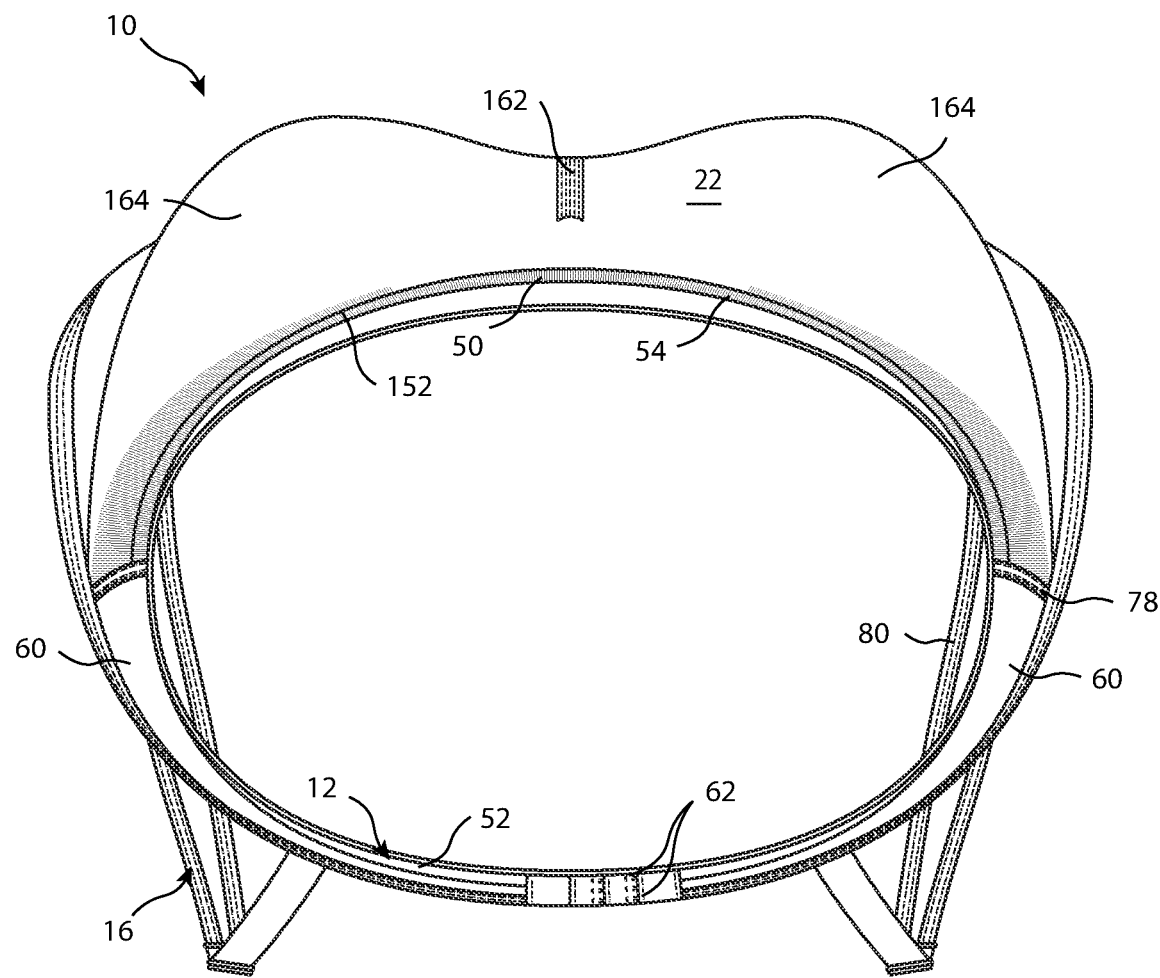
FIG. 10 is a bottom view illustration of the nursing garment of FIG. 4 in the normal wear configuration, according to one embodiment of the present invention
Figure 11:
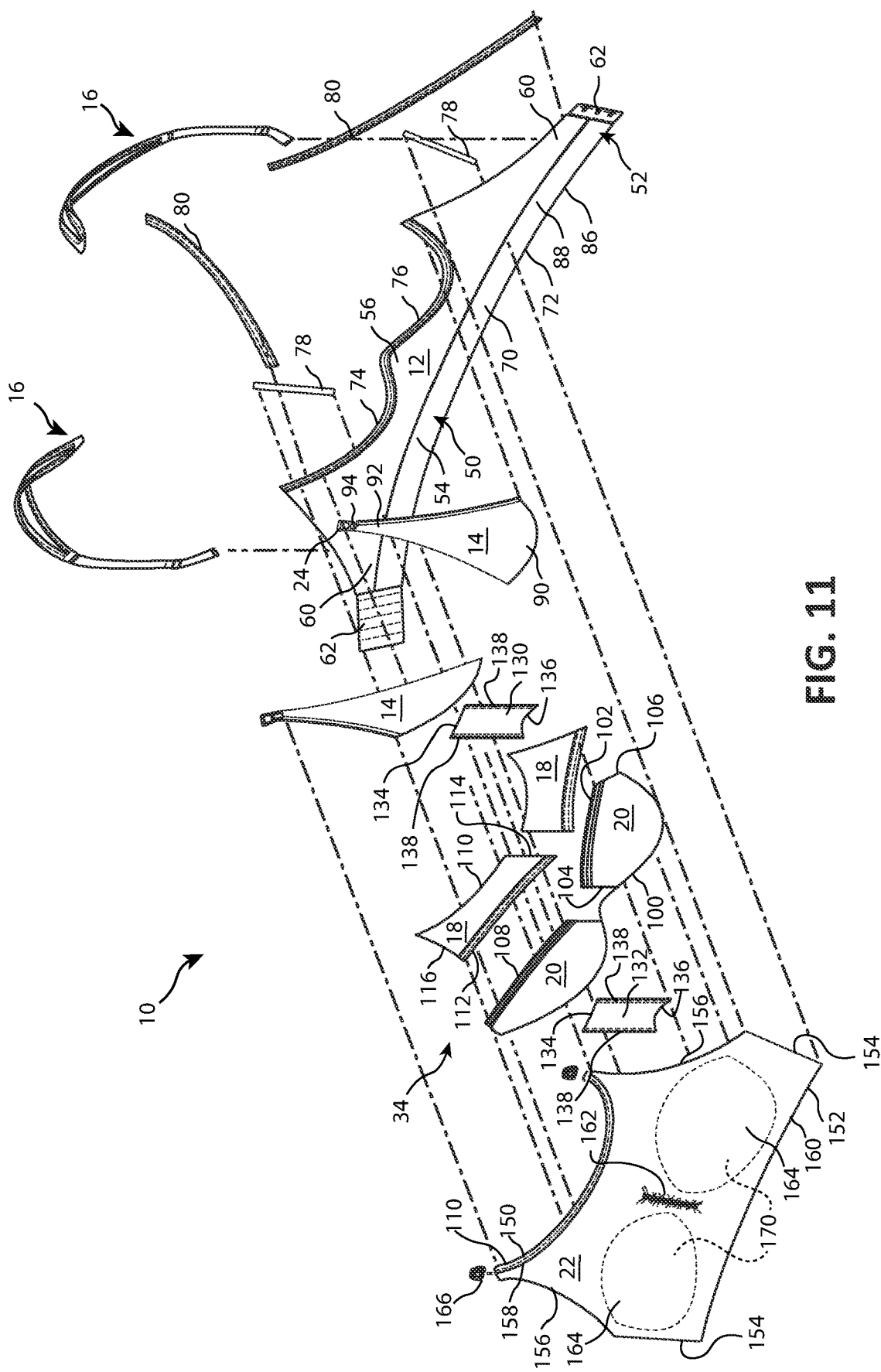
FIG. 11 is a partially exploded, front perspective view of the nursing garment of FIG. 1, according to one embodiment of the present invention.

Bottom retaining panels 18 and top retaining panels 20 are, in one embodiment, each woven with elasticity and resilience to collectively form soft inner cup 34 such that each pair of one of bottom retaining panels 18 and one of top retaining panels 20 receives a breast of wearer 30. The overlap of the pair of bottom retaining panel 18 and top retaining panel 20 forms opening 36 of each soft inner cup 34 such that the two can be pulled apart to extend opening 36 to receiving pump apparatus 40 as shown, for example, with reference to FIGS. 2 and 12. The elasticity of bottom retaining panels 18 and top retaining panels 20 will tightly hold funnel 38 of pump apparatus 40 tightly against breasts 32 for expressing milk from breasts 32 in a hands-free manner, that is, alleviating a need for wearer 30 to continuously hold funnel 38 against their own breasts 32 during milk expression. In one embodiment, each bottom retaining panel 18 is sewn to top retaining panel 20 for a coupling length 122 extending from an underarm portion of nursing garment 10 to add reinforcement to and limit the size of opening 36 as generally illustrated in FIG. 6.

Curved lower edge 100 of bottom retaining panels 18 and curved lower edge 136 of first and second bridge members 130 and 132 are sewn to top edge 74 of band 12, in one example. In one embodiment, exterior ends 106 and 116 of bottom retaining panels 20 and top retaining panels 18 are coupled to each other along their overlap and are secured to each other and band 12 via bindings 80, forming the underarm edge of nursing garment 10 as shown with additional reference to FIG. 12.

Exterior front panel 22 is sized and shaped to selectively cover inner soft cups 34 opposite the torso of wearer 30. In one embodiment, exterior front panel 22 is formed as a single layer of material or a dual layer of a woven fabric having suitable elasticity and resiliency properties. For instance, in one example exterior front panel 22 is formed as a single continuously woven piece of material folded along bottom edge 152 to have two layers. In one embodiment, exterior front panel 22 is formed with a higher modulus of elasticity along a bottom edge portion 160 adjacent to and along bottom edge 152 similar to a bottom portion of band 12. Exterior front panel 22 includes a top or neckline edge 150, a bottom edge 152, opposing side ends 154, and opposing underarm edges 156. Neckline edge 150 is sized and shaped to align with and be coupled to upper edges 110 of retaining panels 18 and top edges 134 of first and second bridge members 130 and 132. In one example, neckline edge 150 is sewn to each of upper edges 110 and 134 via a binding or other construction tape 158 to collectively present to user 30 as a single edge or neckline.

In one embodiment, underarm edges 156 each extend from an opposite end of neckline edge 150 with a curvature designed for comfort of wearer 30 (FIGS. 1-3). Underarm edges 156 each mate or align with the top of a respective one of wings 60 and is secured thereto, for example, with exterior ends 116 and 106 of top retaining panel 18 and bottom retaining panel 20, respectively via binding 80. In this manner, a collectively formed underarm edge, that is formed by exterior front panel 22, top retaining panel 18, and bottom retaining panel 20 and binding 80, is presented as single banded edge for comfort. In one example, each of opposing side ends 154 is secured to a different side of front portion 50 of band 12, for instance, below and secured in part by a length of boning 78, which provides additional stability to nursing garment 10 and support to breasts 32.

To better provide comfort and a good fit, in one example, exterior front panel 22 includes a center elastic strip 162 extending substantially vertically between neckline edge 150 and bottom edge 152 in a substantial center thereof to fit between breasts 32 of wearer 30. Center elastic strip 162 helps define two exterior soft cups 164 of exterior front panel 22 positioned to each overlay one of interior soft cups 34. In one example, such as where exterior front panel 22 is a dual layer construction, removable or permanent pads 170 are incorporated into nursing garment between the dual layers to provide additional modesty, support, etc. to wearer 30.

According to one embodiment, exterior front panel 20 is secured to one of a pair of exterior layer fasteners 166 at an intersection between binding 158 and binding 80. Each of exterior layer fasteners 166 is configured to be selectively coupled, e.g., hooked onto, one of fasteners 94 to selectively couple exterior front panel 22 and inner soft cups 3 to one of the pair of shoulder straps 16 and/or one of the pair of retention straps 14.

In the above-described example configuration, when exterior layer fasteners 166 are coupled with corresponding fasteners 94, inner soft cups 34 and exterior front panel 22 are in place over breasts of wearer 30 as shown with collective reference to FIGS. 1, 2, and 12. When exterior layer fasteners 166 are coupled with corresponding fasteners 94 and exterior front panel 22 lays in place over inner soft cups 34 as shown in FIGS. 1 and 4-10, nursing garment is in the first or normal wear configuration. To express milk from breasts 32 (see FIG. 3), exterior front panel 22 can be lifted upwardly from bottom edge 160, which as described above remains free from coupling between opposing ends thereof to provide access to one or both of inner soft cups 34. One or both of inner soft cups 34 is opened by pulling corresponding ones of bottom free edges 112 of top retaining panel 18 up and corresponding ones of top free edges 102 of bottom retaining panels 20 down to form opening 36 as shown in the left side of FIG. 12 to be in a second or pumping configuration. In a pumping configuration, funnel or shield 38 of pump apparatus 40 can be positioned to fit tightly to one or both of breasts 32 with a neck 42 thereof or other extension extending through opening 36 to allow shield 38 to express milk through neck 42 via pump apparatus 40 as best shown in FIG. 2.

Figure 13:
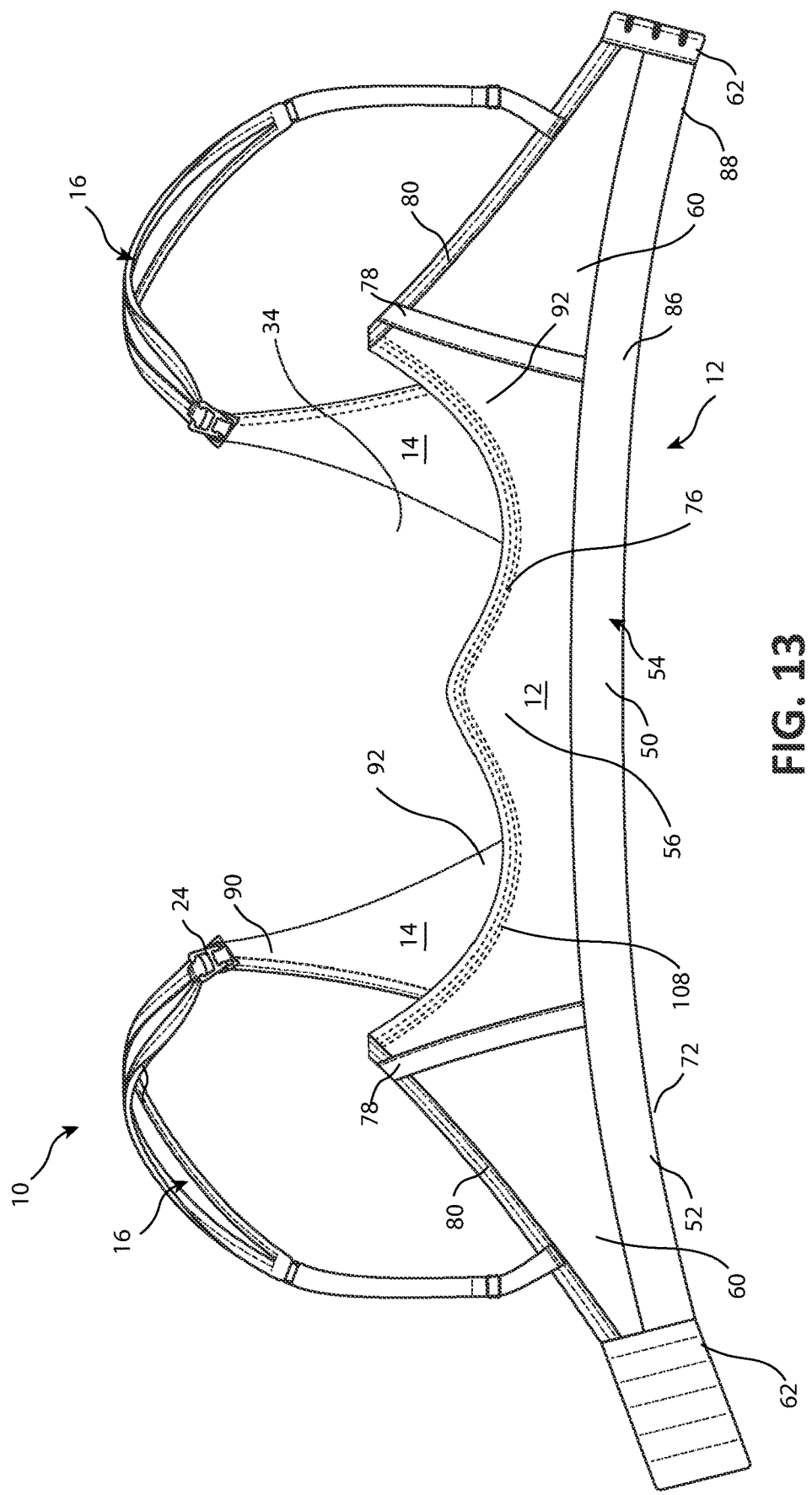
FIG. 13 is a rear view illustration of the nursing garment of FIG. 1 in an open and breast-feeding configuration, according to one embodiment of the present invention.

To expose breasts 32 of wearer 30, for example for direct nursing to a child, bottom free edges 112 of top retaining panels 18 and bottom edge 160 of exterior front panel 22 are not pulled up and corresponding ones of top free edges 102 of bottom retaining panels 20 are not pulled down. Instead, in one embodiment, one or both of exterior layer fasteners 166 are unhooked from fasteners 94 and a portion of or all of exterior front panel 22 and inner soft cups 34 are folded down to expose one of both corresponding breasts 32, for example, as illustrated with reference to FIGS. 3 and 13 in a third or breast-feeding configuration. In this manner, full access to breast 32 allows for unimpeded breast feeding. In one example, even when breasts 32 are exposed. When breast feeding is finished, inner soft cups 34 and exterior soft cups 164 are folded up to fit over breasts 32 and exterior layer fasteners 166 are re-secured to fasteners 94 placing nursing garment 10 back in the normal wear configuration for continued wear.

FIG. 14 shows one embodiment of the present invention, that is, nursing garment 210. Nursing garment 210 is largely like nursing garment 10 (see FIGS. 1-13), but with band 212 extending further downwardly to substantially cover the torso of wearer 30 below breasts 32. Band 212 is, in one embodiment, otherwise substantially identical to band 12. In other embodiments, the extension below breasts 32 may be formed by a separate material or extension. In one example, lower perimeter section 70 is extended and/or is not formed with the extra elastic as compared to a remainder of band 212. While shown only in the normal wear configuration in FIG. 14, one of skill in the art will understand that nursing garment 210 is convertible between the expressing and breast-feeding configurations in a similar manner as described above for nursing garment 10. Other variations and adjustments to either one or both of nursing garments 10 and 210 will be apparent to those of skill in the art upon reading the present application.

Although the invention has been described with respect to particular embodiments, such embodiments are meant for the purposes of illustrating examples only and should not be considered to limit the invention or the application and uses of the invention. Various alternatives, modifications, and changes will be apparent to those of ordinary skill in the art upon reading this application. Furthermore, there is no intention to be bound by any theory presented in the preceding background of the invention or the above detailed description.

What is claimed is:

1. A nursing garment configured to be worn by a wearer having breasts and for periodic use with a pumping apparatus, the nursing garment comprising:
a band configured to extend around a torso of the wearer below the breasts;
a pair of inner soft cups secured near a top edge of the band, wherein each of the pair of inner soft cups includes a top retaining panel and a bottom retaining panel, which is separate from the top retaining panel, overlapping one another across a substantially horizontal length of a corresponding one of the pair of inner soft cups, the top retaining panel and the bottom retaining panel being configured to be selectively pulled away from each other to form an opening therebetween to permit a portion of the pumping apparatus to extend through the opening facilitating the expression of milk from the breast via the pumping apparatus; and
an exterior front panel extending over the pair of inner soft cups wherein the exterior front panel defines a bottom edge that is free from mid-length securement such that the exterior front panel is configured to selectively be at least partially pulled upwardly away from the band to expose one or both of the pair of inner soft cups.

2. The nursing garment of claim 1, wherein:
the band includes an under-cup binding along a portion of the top edge of the band, the under-cup binding being secured to the band in a W-shape and to extend under the breasts of the wearer when nursing garment is worn by the wearer, and
the bottom retaining panel is coupled to the under-cup binding along the portion of the top edge of the band and extending upwardly from the under-cup binding.

3. The nursing garment of claim 2, wherein:
the bottom retaining panel defines an upper edge opposite the under-cup binding having a substantially free length between opposing ends of the bottom retaining panel adjacent the opening, and
the upper edge of the bottom retaining panel selectively extends above a bottom of the top retaining panel and is configured to be selectively pulled down below the bottom of the top retaining panel to permit the portion of the pumping apparatus to extend through the opening.

4. The nursing garment of claim 1, wherein the top retaining panel and the bottom retaining panel are coupled along exterior edges thereof to one of two underarm edges of the exterior front panel.

5. The nursing garment of claim 4, wherein:
the band includes an under-cup binding along a portion of the top edge of the band, the under-cup binding being secured to the band in a W-shape and to extend under the breasts of the wearer when nursing garment is worn by the wearer, and
the bottom retaining panel is coupled to the under-cup binding along the portion of the top edge of the band and extending upwardly from the under-cup binding.

6. The nursing garment of claim 5, wherein:
the bottom retaining panel defines an upper edge opposite the under-cup binding having a substantially free length between opposing ends of the bottom retaining panel adjacent the opening, and
the upper edge of the bottom retaining panel selectively extends above a bottom of the top retaining panel and is configured to be selectively pulled down below the bottom of the top retaining panel to permit the portion of the pumping apparatus to extend through the opening.

7. The nursing garment of claim 4, wherein:
the exterior front panel defines a neckline edge opposite the bottom edge of the exterior front panel extending between the two underarm edges of the exterior front panel, and
the top retaining panel includes an upper edge and a lower edge opposite the upper edge with the upper edge of the top retaining panel being secured to the exterior front panel along the neckline edge thereof.

8. The nursing garment of claim 7, wherein:
the exterior front panel additionally comprises two underarm edges spaced from one another,
a first fastener is secured to the exterior front panel near an intersection of the neckline edge and a corresponding one of the two underarm edges,
a strap extends from the band and is coupled to a second fastener configured to be selectively coupled with the first fastener to hold the exterior front panel to extend upwardly away from the band over the pair of inner soft cups.

9. The nursing garment of claim 8, wherein the exterior front panel additionally comprises opposing ends each extending from the corresponding one of the two underarm edges to the bottom edge of the front panel, and each of the opposing ends of the exterior front panel is sewn to the band.

10. The nursing garment of claim 9, wherein the lower edge includes a portion bordering the opening that is at least partially free from direct securement to the exterior front panel and the bottom retaining panel.

11. The nursing garment of claim 10, further comprising:
a retention strap extending upwardly from near an end of the under-cup binding and being secured to the second fastener and the shoulder strap.

12. The nursing garment of claim 11, wherein the retention strap is configured to extend along a side of one of the breasts for support and is tapered as it extends from the under-cup binding to the second fastener.

13. The nursing garment of claim 12, wherein one of the pair of inner soft cups extends over the retention strap opposite the wearer.

14. The nursing garment of claim 7, further comprising a length of boning extending along the coupling between one of the opposing ends of the exterior front panel and the band to add stability to the nursing garment.

15. The nursing garment of claim 1, wherein:
the exterior front panel additionally comprises:
a neckline edge opposite the bottom edge, and
two underarm edges extending from opposing ends of the neckline edge, and
the nursing garment additionally comprises:
a first fastener secured to the exterior front panel near an intersection of the neckline edge and a corresponding one of the two underarm edges, and
a shoulder strap extends upwardly and forwardly from a rear of the band and is coupled to a second fastener that is configured to be selectively coupled with the first fastener to hold the exterior front panel to extend upwardly away from the band over the pair of inner soft cups.

16. The nursing garment of claim 15, wherein the exterior front panel additionally comprises opposing ends each extending from the corresponding one of the two underarm edges to the bottom edge of the front panel, and each of the opposing ends of the exterior front panel is sewn to the band.

17. The nursing garment of claim 1, wherein:
the nursing garment is convertible between a normal wear configuration, a pumping configuration, and a nursing configuration all while being worn by the wearer,
in the normal wear configuration, the pair of inner soft cups extend over the retention straps and the breasts of the wearer, and the exterior front panel extends over and covers the pair of inner soft cups,
in the pumping configuration, the exterior front panel is at least partially pulled away from the band to expose the opening in the pair of inner soft cups, and
in the nursing configuration, the pair of inner soft cups and the exterior front panel are folded down toward the band to expose the retention strap and the breasts of the wearer.

18. The nursing garment of claim 17, further comprising:
a retention strap extending upwardly from the band to be positioned on an outer side of one of the breasts of the wearer in each of the normal wear configuration, the pumping configuration, and the nursing configuration; and
a shoulder strap extending from an end of the retention strap opposite the band to a rear portion of the band.

19. The nursing garment of claim 18, wherein the retention strap is configured to extend along a side of one of the breasts for support, is tapered as it extends from the band to the shoulder strap, and covers an inner soft cup of the pair of inner soft cups when the nursing garment is in the wear configuration and in the pumping configuration.

20. The nursing garment of claim 19, wherein:
the exterior front panel additionally comprises a neckline edge opposite the bottom edge of the exterior front panel and two underarm edges extending away from opposite ends of the neckline edge,
the nursing garment further comprises:
a first fastener secured to the exterior front panel near an intersection of the neckline edge and a corresponding one of the two underarm edges, and
a second fastener secured to the shoulder strap and the retention strap in a manner coupling the strap to the retention strap, and
where the first fastener is coupled to the second fastener in the normal wear configuration and the pumping configuration and is uncoupled from the second fastener in the nursing configuration.

21. The nursing garment of claim 1, wherein the top retaining panel is directly secured to the bottom retaining panel along a length of an overlap between the top retaining panel and the bottom retaining panel extending away from the opening.

22. The nursing garment of claim 1, wherein the top retaining panel includes an upper edge and a lower edge opposite the upper edge, the upper edge of the top retaining panel being secured to the exterior front panel along a neckline edge thereof.

* * * * *